United States Patent
Schillers et al.

(10) Patent No.: US 7,160,729 B2
(45) Date of Patent: Jan. 9, 2007

(54) METHOD FOR DETECTING DISEASES THAT ARE ASSOCIATED WITH DEFECTS OF CYSTIC FIBROSIS TRANSMEMBRANE CONDUCTANCE REGULATOR (CFTR) PROTEIN

(76) Inventors: Hermann Schillers, Castelleweg 7, 48155 Münster (DE); Hans Oberleithner, Hittorferstrasse 41, 48149 Münster (DE)

( * ) Notice: Subject to any disclaimer, the term of this patent is extended or adjusted under 35 U.S.C. 154(b) by 0 days.

(21) Appl. No.: 10/505,828

(22) PCT Filed: Feb. 25, 2003

(86) PCT No.: PCT/EP03/01904

§ 371 (c)(1),
(2), (4) Date: May 13, 2005

(87) PCT Pub. No.: WO03/073103

PCT Pub. Date: Sep. 4, 2003

(65) Prior Publication Data

US 2005/0221273 A1     Oct. 6, 2005

(30) Foreign Application Priority Data

Feb. 26, 2002   (DE)  ................................ 102 08 293
Apr. 12, 2002   (DE)  ................................ 102 16 160

(51) Int. Cl.
*G01N 33/48*     (2006.01)
*C12Q 1/00*     (2006.01)

(52) U.S. Cl. .................... 436/63; 435/2; 435/4; 435/29
(58) Field of Classification Search ................. 436/63; 435/2, 4, 29; 514/184
See application file for complete search history.

(56) References Cited

OTHER PUBLICATIONS

Braunstein et al. The Journal of Biological Chemistry, vo. 276, No. 9, Mar. 2, 2001,pp. 6621-6630.*
Bronsveld et al. The Journal of Clinical Investigation, vol. 108, No. 11, Dec. 2001, pp. 1705-1715.*
Reddy et al. Journal of Membrane Biology, vol. 189, 2002, pp. 15-25.*
Schultz et al. Physiological Reviews, vol. 79, suppl., No. 1, Jan. 1999, pp. S109-S144.*
Suleymanian et al. Journal of Molecular and Cellular Cardiology, vol. 27, 1995, pp. 721-728.*

* cited by examiner

*Primary Examiner*—Maureen M. Wallenhorst
(74) *Attorney, Agent, or Firm*—Thorpe North & Western, LLP

(57) ABSTRACT

The invention concerns a method for the diagnosis of membrane channel defects in cells by comparing defective with non-defective cells with the following steps: influencing the volume regulation of the cells; recording the change of volume regulation resulting therefrom in non-defective cells; determining the existence of defective cells with a volume change deviating therefrom, in order to provide a suitable method which enables the identification of diseases based on CFTR defects, in particular cystic fibrosis, at an early stage.

22 Claims, 6 Drawing Sheets

Fig. 1
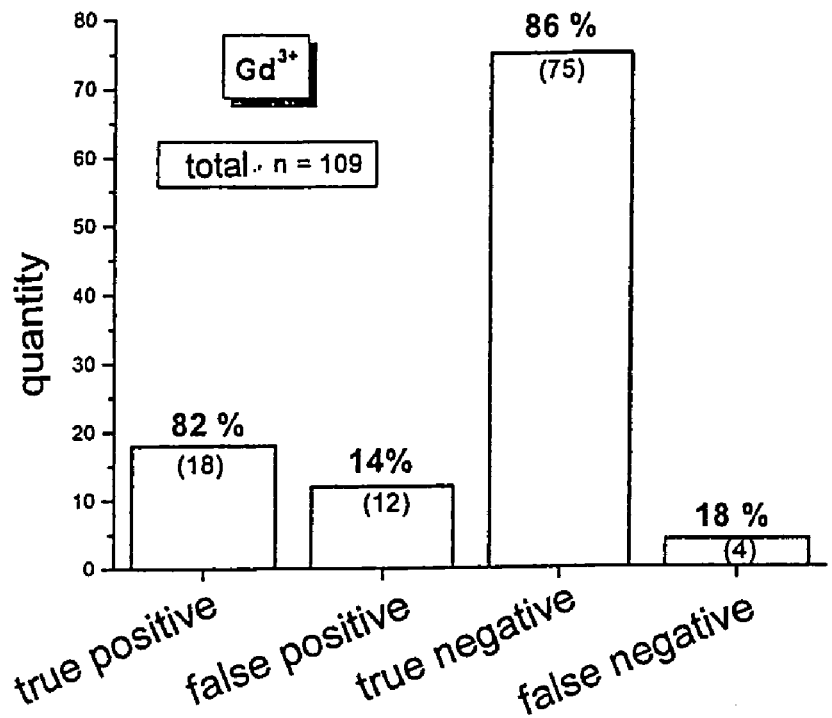
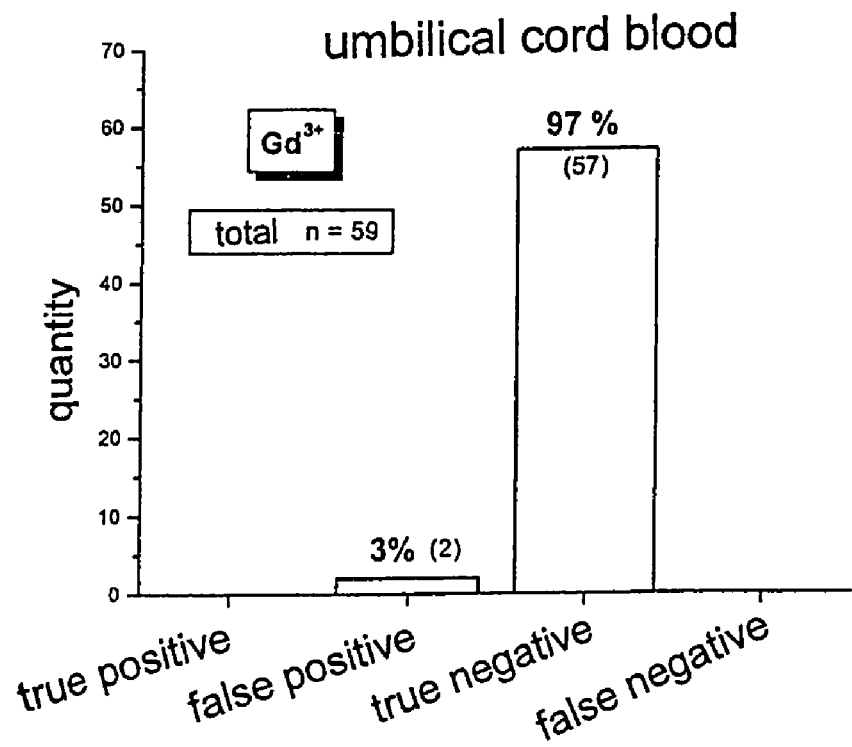

Fig. 2
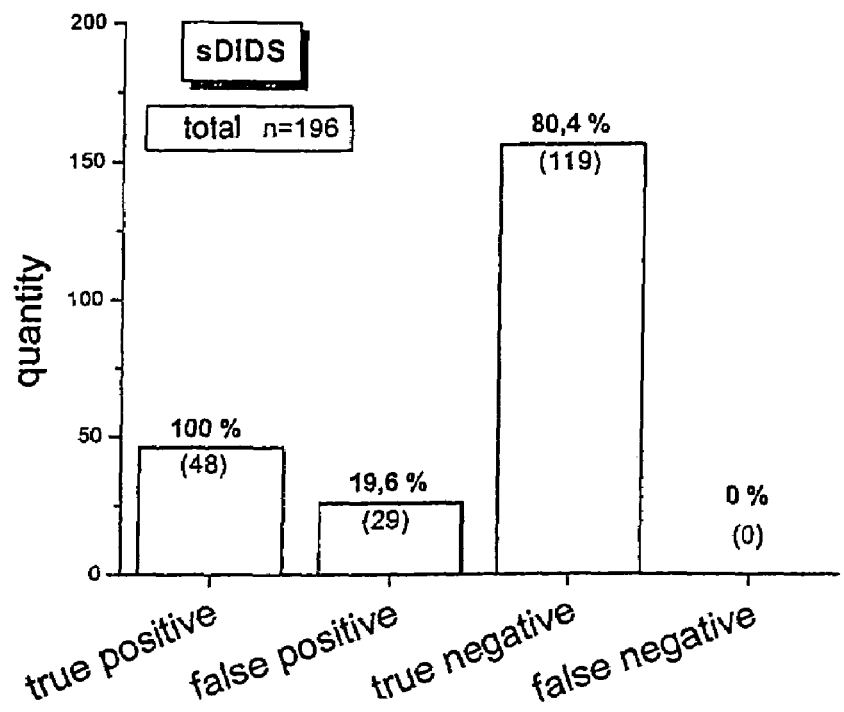
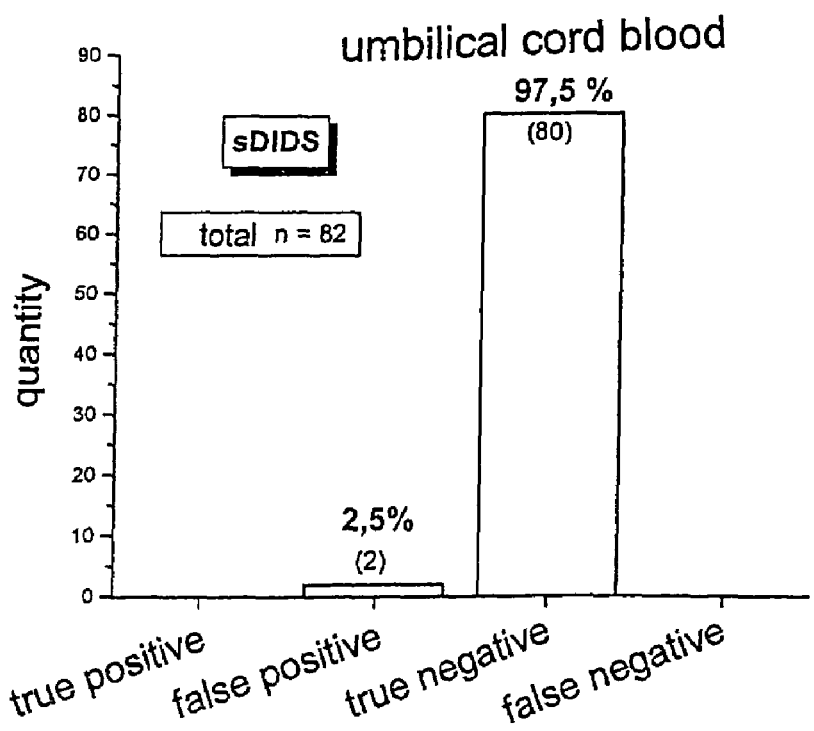

Figure 3:
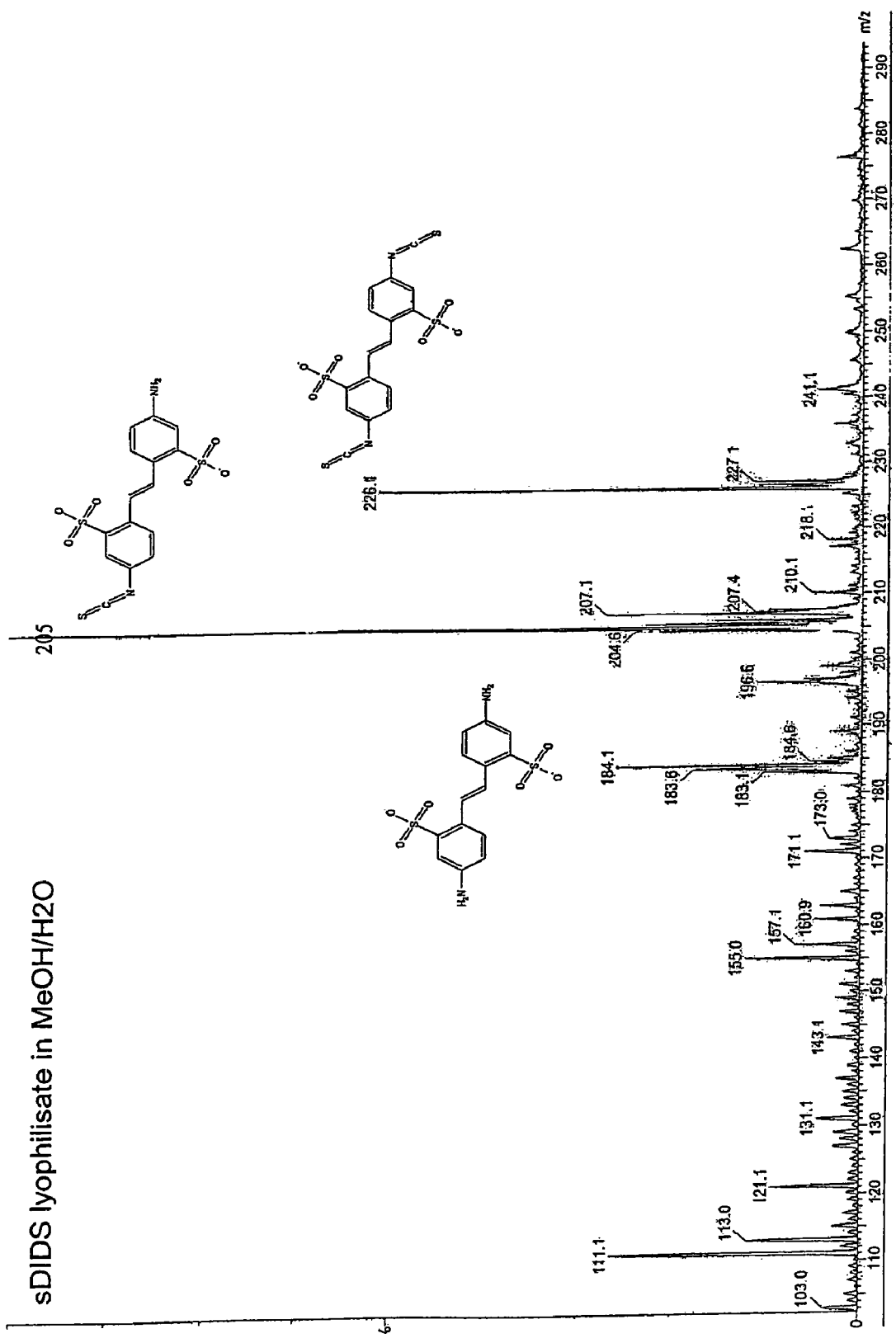

Fig. 3 sDIDS lyophilisate in MeOH/H2O 4,4'-diisothiocyanato-stilbene-2,2'-disulfonic acid, Na$^+$-salt (DIDS)

4-amino-4'-isothiocyano-stilbene-2,2'-disulfonic acid, Na$^+$-salt 4-acetamido-4'-isothiocyano-stilbene-2,2'-disulfonic acid, Na$^+$-salt (SITS)

4-amino-4'-isothiocyano-stilbene-2,2'-disulfonic acid, Na$^+$-salt

METHOD FOR DETECTING DISEASES THAT ARE ASSOCIATED WITH DEFECTS OF CYSTIC FIBROSIS TRANSMEMBRANE CONDUCTANCE REGULATOR (CFTR) PROTEIN

The invention concerns non-genetic verification procedures and means for illnesses that are based on defects of the CFTR, in particular for the illness mucoviscidosis (cystic fibrosis or CF) and claims priority of the German patent applications 102 08 293.6 and 102 16 160.7 (incorporated herein by reference).

Different diseases based on defects of the CFTR, for example cystic fibrosis, the congenital absence of the vas deferens, and some forms of pancreatitis, are well-known. Cystic fibrosis—also known as mucoviscidosis—represents one of the most frequently occurring genetically caused illnesses. The illness appears in regionally varying frequency of approx. 1:2500 newborn children.

Mucoviscidosis is autosomal recessive and arises from a defect at the long arm of chromosome 7. The gene that encodes the protein CFTR (cystic fibrosis transmembrane conductance regulator), a membrane transport protein, is affected. The main symptom of this serious illness is a general lack of function of the epithelia, all exocrine glands, the lung and the digestive tract. The illness expresses itself by an increased viscosity of the mucous secretions of the glands in the lung and in the pancreas. In the progressive illness, substantial anatomical changes occur, with the consequence of severe complications in the region of the respiratory system, as for example chronic infections with emphysema of the lung and serious disturbances of digestion (malabsorption) with liquid and electrolyte losses. Treatment of cystic fibrosis takes place via enzyme substitution, specific antibiotic and physiotherapeutic treatment (percussion massage). The illness is not curable. Mucoviscidosis patients suffer from a substantial restriction of their quality of life and as a rule, reach an age of only approx. 40 years despite today's good medical support.

The disease emergence is not clearly clarified yet. The affected gene codes for a chloride channel located predominantly in the membrane of epithelial cells. A multiplicity of different mutations, which lead to increased mucus viscosity and a changed composition of the secretions, is described (Pschyrembel, Clinical Dictionary, 258th Edition). The most frequent mutation is the deletion of phenylalanin at position 508 (dF508). Beside the homozygote form of the mucoviscidosis, the illness can also develop with heterozygote genetic carriers with varying severity level and also can develop at an advanced age. About 4% of the white population of Europe and the USA carry a heterozygote CFTR mutation.

From the literature it is well-known that with CF patients with the dF508 homozygote mutation, the CFTR protein in the plasma membrane of the cells is either not achieved or is insufficiently anchored in the membrane. Such a CFTR protein is then nonfunctioning.

From the literature it is further well-known that the CFTR has a substantial influence on the regulation of the cell volume. In cells, in which the CFTR function is not disturbed, it encroaches on an autocrine mechanism, which is steered by the release of and the signal transmission by ATP (adenosine triphosphate) through a separate ion channel. A hypotonic medium causes a water influx directed inward to the cell. The cell swelling resulting from it activates the CFTR that again releases an ATP transport from the cell. The extracellular ATP activates purinergic receptors, which energize the phospolipase C (PLC) in the line for the formation of inositol triphosphate ($IP_3$). The inositol triphosphate increases the intracellular concentration of calcium ions ($Ca^{2+}$). A increased intracellular calcium ion concentration activates the calcium-dependent potassium and chloride channels as well as channels for osmolytes, for example Taurin. Thereupon potassium and chloride ions leave the cell. Because of this net salt loss water flows osmotically backwards. As a consequence the cell shrinks (Braunstein, G. B. et al. The Journal of Biological Chemistry, volume 276, No. 9. Issue of March 2, pp. 6621–6630, 2001). This process is designated regulatory volume decrease (RVD). It was shown that the release of ATP from human red blood cells after mechanical deformation is dependent on CFTR. (Sprague R S, Ellsworth M L, Stephenson A H , Kleinhenz M E, Lonigro A J, deformation induced ATP release from red blood cells requires cystic fibrosis transmembrane conductance regulator activity. American Journal of Physiology, 275:H172M1732, 1988). It was shown that in hypotonic media the red blood cells of some species regulate their volume depending on ATP; however, not human red blood cells. (Light D S, Capes T L, Gronau R T, Adler M R. Extracellular ATP stimulates volume decrease in Necturus red blood cell. American Journal of Physiology, Sep; 277(3 Pt 1):C480-01. 1999).

Methods of CF Diagnosis:

1) Until now the diagnosis of cystic fibrosis is accomplished, among other methods, by a sweat test in which the CFTR dependent chloride absorption of the epithelium cells of the sweat ducts is determined by measurement of the chloride concentration in the sweat (Patent-Nr.: WO00/13713 title: Macroscopic sweat test for cystic fibrosis). With CF patients an increased chloride concentration is found. The sweat test is only practicable starting from the 4$^{th}$ month of life, and frequently provides unclear results. Besides, it is very time consuming and complex for personnel and thus expensive.

2) Other methods are the measurement of the immunoreactive trypsin introduced by the pancreatic insufficiency of CF patients into the blood (Patent No.: AU 6445186. Title: Detection of immunoreactive trypsin and cystic fibrosis using monoclonal antibody) and 3) the verification of an increase of the albumin content in the meconium (infant fecal material) of babies (patent No.: U.S. Pat. No. 3,902,847, title; Diagnostic Device and Method for the Diagnosis of mucoviscidosis (cystic fibrosis)).

4) In addition, CF diagnosis can be made by the investigation of salivary gland secretion and by 5) the exact, but complex, and thus so far little applied, transepithelial nasal potential measurement of the nasal mucus membrane.

6) A further possibility for the diagnosis of cystic fibrosis exists in the recognition of the mutation by direct gene analysis (Patent-No.; W094/15216. title: Detection of cystic fibrosis or a gene mutation). The genetic investigation certainly allows only very limited conclusions regarding functional disturbances. There are, so far, many hundred different CFTR mutations well-known, which lead to more or less defined clinical images. In the genetic analyses, however, only approx. 15 different mutations are examined, which cause only about 80 of all CF illnesses.

7) There was a CF test motivated, in which ATP released by erythrocytes through mechanical deformation was to be measured with a luciferase assay. This is based on the observation of a relationship between CFTR and ATP secretion. (Verloo. P. et al., Pediatric Pulmonology. Suppl. 20:72 (2000)).

8) Other methods are based on differences between CF and non-CF in kinetics of some enzymes, e.g. the NADH dehydrogenase of mitochondria (Patent No.: PCT/US8Q/00370, title: Cystic fibrosis detection method), which can be measured e.g. in the lymphocyte homogenate.

9) The enzyme hydrolase of CF patients shows faster inactivating kinetics than the hydrolase of healthy test subjects (patent No.: U.S. Pat. No. 4,489,788, Title: In vitro diagnosis of cystic fibrosis).

The well-known test procedures are somewhat expensive and have the disadvantage that they offer little reliability and thus no reliable newborn screening for mucoviscidosis. Genetic testing is possible with newborn children, but with heterozygote mutations permits no statement about the functional extent of the CFTR defect. The sweat test is practicable starting from the 4th month of life and is connected with substantial fluctuations. The measurement of the immunoreactive trypsin and the measurement of the albumin in the meconium are not very reliable.

By a diagnosis accomplished as early as possible—most effectively with the newborn child—a purposeful treatment starting from the first life day could improve the health situation of the patients, and thus clearly increase the life expectancy, and in this case the serious, illness-caused anatomical changes would develop less strongly.

Since the standard techniques do not permit an early diagnosis of cystic fibrosis, CF illnesses can be surely recognized only at a late point in time. In clinical practice, babies in justified cases of suspicion are especially treated with antibiotics, which causes expense and can lead to health impairments. With the heterozygous CF mutation, it is possible that the illness in its varying degrees of severity manifests itself first in youth or even later in adulthood excluding successful early treatment. Furthermore, there are clinical pictures, for example certain pancreatic illnesses, that are supposed to be associated with mutations of the CFTR gene.

It is the objective of the invention to provide a suitable method to reliably detect illnesses that are based on defects of the CFTR, especially cystic fibrosis, as early as possible.

This objective is achieved by a diagnosis method which is based on the destabilization of the CFTR dependent volume regulation of the cells obtained from a patient and subsequently determining either the volume increase or the lysis of the so obtained cells. According to the invention, the identification is possible, e.g., by prevention of the CFTR-dependent volume regulation by, for example, blockade of the ATP release, or through activation (opening) of CFTR-dependent ion channels of the non-defective cells.

An example of a test procedure in accordance with the invention:

A non-defective cell is able to control and regulate its cell volume by interlinking mechanisms during the influx and the efflux of ions and water under physiological conditions. In non-defective blood cells, after application of a 155 mm potassium chloride medium chloride flows into the cell, inter alia through the CFTR. In one embodiment, the invention is based on the idea to inhibit the regulatory volume decrease (RVD) by influencing—for example by blockade—the CFTR-dependent ATP-transporting channels expressed in the cytomembrane. Inflowing potassium and chloride ions accumulate in the functional non-defective cell, which, because of the accompanying water inflow, leads to lysis of the blood cells, while a lysis of defective blood cells that lack the inward transport of the ions does not occur. This is especially the case with CF blood cells, which due to the CFTR defect have no influx of chloride ions and whose RVD is independent of CFTR. Therefore, no positive pressure can build up in the cell; the blood cells with defective ion channels, especially the blood cells of CF patients undergo no lysis.

In patients suffering from mucoviscidosis with a homozygous ΔF508 mutation, the CFTR is not in the cytomembrane. With heterozygous mutations and other mutations than ΔF508, small quantities of functional CFTR can be in the membrane that transport chloride and are involved in volume regulation. The quantity of the functional CFTR molecules in the cytomembrane is inversely proportional to the severity of the illness. The CFTR dependent RVD is inhibited by the blockade of the CFTR dependent ATP transporting channels. The contribution of the CFTR dependent RVD to the entire RVD is proportional to the quantity of the functional CFTR molecules within the membrane. The more CFTR in the membrane, the bigger the contribution of the CFTR dependent RVD is to the entire RVD and the greater is the hemolysis after blockade of the CFTR dependent RVD. Therefore, the degree of the hemolysis after blockade of the CFTR dependent RVD is a measurement of the functional CFTR molecules in the cytomembrane. Because the quantity of the functional CFTR molecules in the cytomembrane is inversely proportional to the severity of the illness in mucoviscodosis patients, the degree of the hemolysis after blockade of the CFTR dependent RVD is a measurement for the severity of the illness.

Examinations of the blood of healthy people, mucoviscidosis patients, and blood samples taken postnatal from the umbilical cord of newborns (umbilical cord blood) confirms the easy practicability and the significance of the test procedure, in which $Gd^{3+}$ is used for blockade of the volume regulation. The statistical evaluation of the past findings of an investigation with 22 CF patients and 87 healthy volunteers as well as 59 newborns (using umbilical cord blood) shows an unambiguous increase of the degree of hemolysis after addition of $Gd^{3+}$ with the healthy volunteers and with the umbilical cord-blood. With the CF patients, only a slight increase of the degree of hemolysis is recorded after $Gd^{3+}$ application. Among the 87 healthy volunteers, 75 were identified as non-CF, i.e., true negative (86%); and 12 were identified as CF, i.e., false positive (14%). With the 22 CF patients, 18 were identified as CF, i.e., truly positive (82%), and 4 were identified as non-CF, i.e., false negative (18%). 57 of the 59 newborns were identified as non-CF, i.e. truly negative (97%), and 2 were identified as CF, i.e. false positive (3%) (FIG. 1).

Example of a test method according to another embodiment of the invention for blood cells:

The objective is accomplished by a diagnosis method that is especially suitable to diagnose CFTR-based illnesses. This method allows the diagnosis of defective blood cells by identifying non-defective blood cells by the activation (opening) of certain ion channels of the non-defective blood cells.

This embodiment of the invention is based on the idea of evoking a lysis of the non-defective blood cells through activation of certain ion channels of the non-defective blood cells, where through anions flow into the non defective cell, for example: Iodide (I—), bromide (Br—), chloride (Cl—), fluoride (F—), gluconate (dextronic acid-anion), rhodanate (SCN—), and taurine. In defective blood cells these CFTR dependent ion channels don't exist or are not activatable. Therefore, the influx of anions as, for example: iodide, bromide, chloride, fluoride, gluconate, rhodanate and taurine into the defective cell does not occur. Then no positive pressure can build up in the cell; the blood cells with defective CFTR, especially the blood cells of CF Patients are not subject to lysis.

Since this CFTR dependent ion channel in non-defective blood cells allows the passage of anions such as for example: iodide, bromide, chloride, fluoride, gluconate and rhodanate as well as taurine, the differentiation between defective and non-defective blood cells can also take place in 155 mm solutions that contain iodide, bromide, fluoride, gluconate, rhodanate or taurine.

The blood cells with defective ion channels, especially the blood cells of CF-Patients, are not subject to lysis.

The statistical evaluation of the examination findings among 48 CF patients and 148 healthy volunteers as well as 82 newborns (umbilical cord-blood) shows an unambiguous increase of the degree of hemolysis after addition of sDIDS, (4-amino-4'-isothiocyanato-stilbene-2,2'-disulfonic acid, herein after referred to as sDIDS), among the healthy volunteers and with the umbilical cord-blood. With the CF patients, only a slight increase of the degree of hemolysis can be recorded after sDIDS application. Among the 148 healthy volunteers, 119 were identified as non-CF, i.e. true negative, 80.4%), and 29 were identified as CF, i.e. false positive, 19.6%). Among the 48 CF patients, all 48 were identified as CF, i.e. true positive, 100%). 80 were identified among the 82 newborns as non-CF, i.e. true negative, 97.5%), and 2 were identified as CF, i.e. false positive, 2,5%), FIG. 2.

The activation of certain CFTR dependent ion channels, which allows the passage of anions such as, for example: iodide, bromide, chloride, fluoride, gluconate, rhodanate and taurine, is possible with a substance that originates from DIDS (4,4'-diisothiocyanato-stilbene-2,2'-disulfonic acid, sodium salt) having undergone a special treatment. DIDS is dissolved in DMSO (0,1 M) and stored for 4 weeks at 4° C. in the refrigerator. Through this storage of DIDS, a hydrolysis-product of DIDS emerges through the residual water contained within the DMSO. Analysis of this solution with mass spectrometric methods shows that besides DIDS, also 4,4'-diamino-stilbene-2,2'-disulfonic acid (DADS) and 4-amino-4'-isothiocyanato-stilbene-2,2'-disulfonic acid exist in the solution (FIG. 3).

Through partial hydrolysis of DIDS, the 4-amino-4'-isothiocyanatostilbene-2,2'-disulfonic acid, $H_2S$ and $CO_2$ develops (FIG. 4):

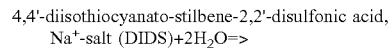

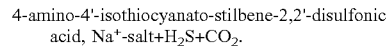

Figure 5:
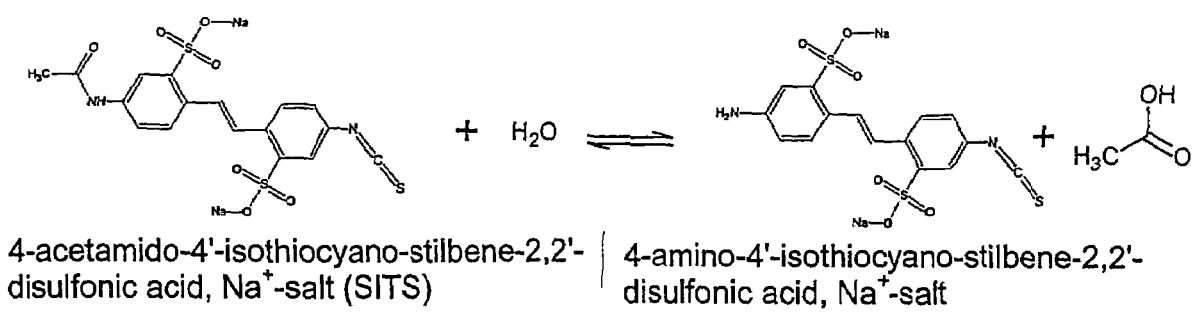

Storage of 4-acetamido-4'-isothiocyanato-stilbene-2,2'-disulfonic acid (SITS) in hydrous DMSO at 4° C. for four weeks leads to hydrolysis products as well, so that also DADS and 4-amino-4'-isothiocyanato-stilbene-2,2'-disulfonic acid are to be found in such a solution as well as SITS. Through partial hydrolysis of SITS, 4-amino-4'-isothiocyanato-stilbene-2,2'-disulfonic acid and acetic acid are to be found (FIG. 5):

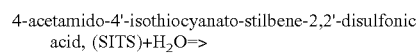

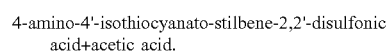

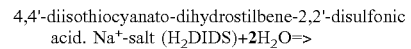

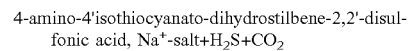

Figure 7:
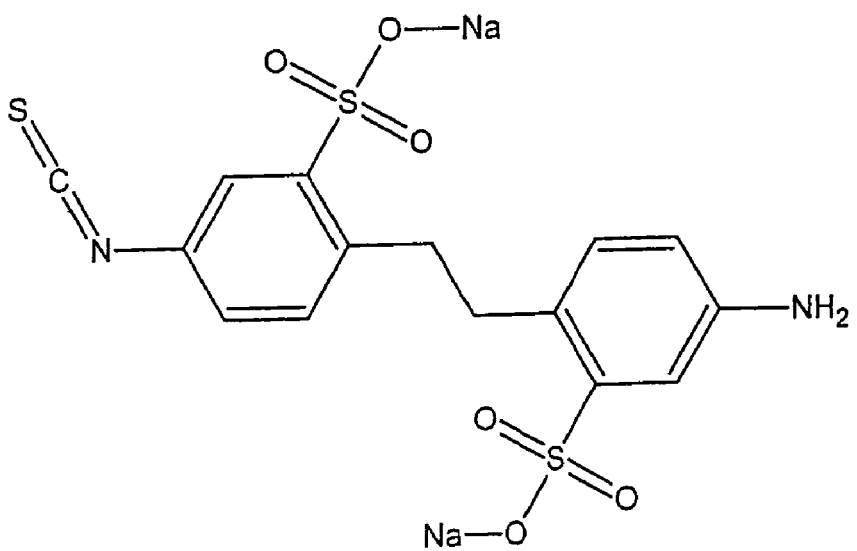

The structure-formula is shown in FIG. 7.

Figure 6:
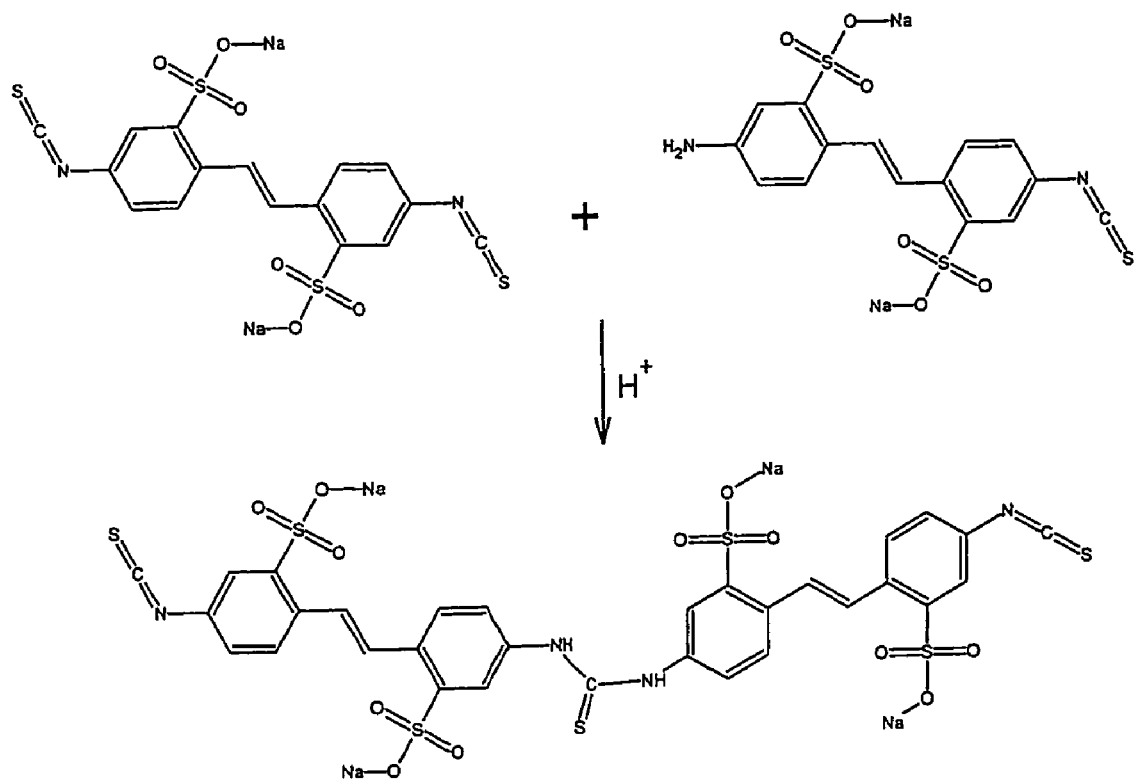

It was described in 1987 by Horobin, Payne and Jakobsen (Horobin R W, Payne J N, Jakobsen P. Histochemical implications of the biological properties of SITS and some related compounds. Journal of Microscopy, 1987 April; 146(1):87–96), that SITS and DIDS transform in aqueous solution through hydrolysis of the acetamido group, e.g. an isothiocyanate group, to 4-amino-4'-isothiocyanatostilbene-2,2'-disulfonic acid. This occurs at room temperature within a week. After three weeks, the DADS has formed through hydrolysis of the remaining isothiocyanate group. With storage of DIDS or SITS in DMSO over several days at room temperature, polymers are formed through reaction of the isothiocyanate groups with amino groups (FIG. 6). In the literature, the polymer formation of the DIDS is described (Schultz B D, Singh A K, Devor D C. BRIDGES R J. Pharmacology of CFTR chloride channel activity. Physiol Rev. 1999 January; 79 (1 Suppl): S109-44s. Review).

Figure 8:
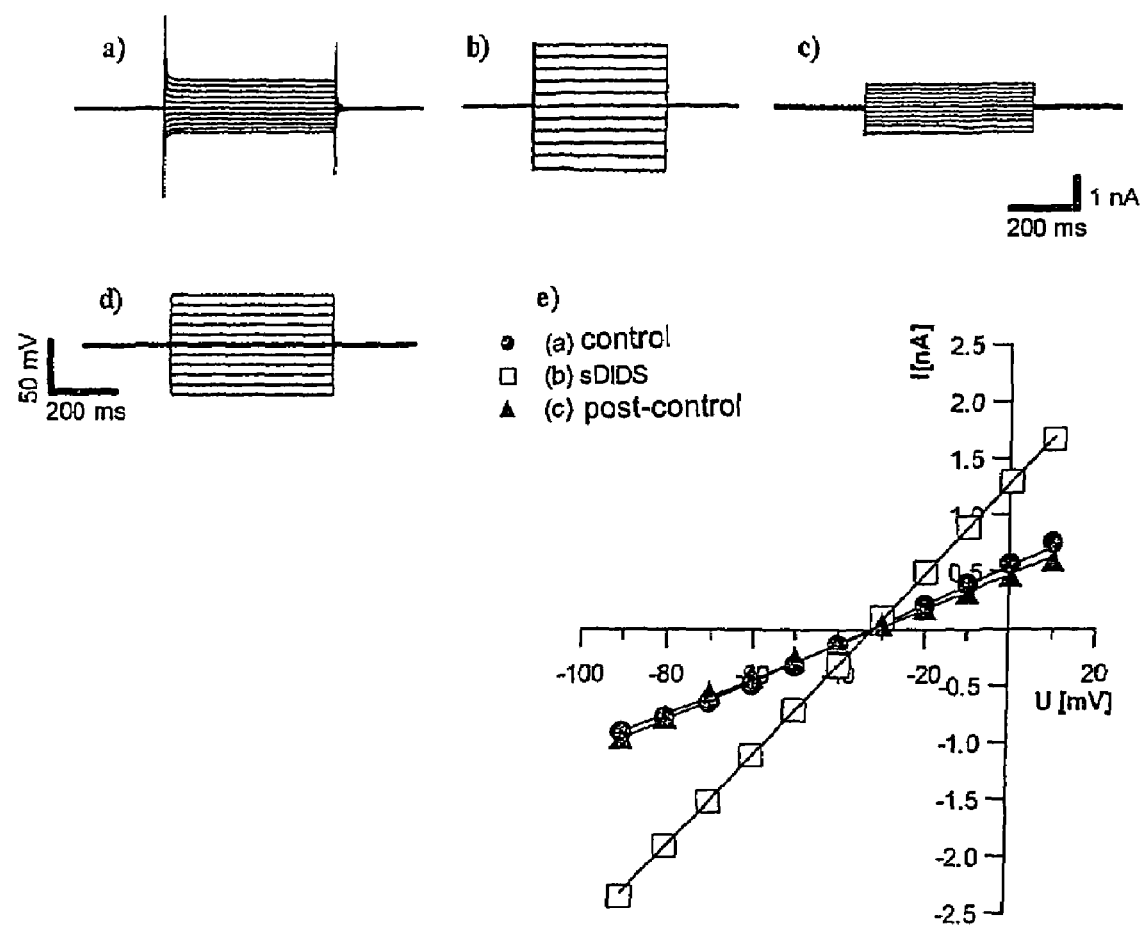

During the experimental development of the test, it is shown that the observed reaction of the red blood cells can not be explained by the mechanisms known in the literature. The blood cell reactions are only explainable by the existence of a channel proteins, which is not yet known in literature. By means of patch-clamp technology, the reversible activatibility of a conductivity (channel protein) through sDIDS could be observed at a human respiratory tract-epithelium-cell-line (Calu-3) in the whole-cell-configuration (FIG. 8).

In the whole-cell-configuration of the patch-clamp technology, the transmembrane current of a cell is measured with a pre-determined potential. The endocellular potential was maintained for 0.5 seconds in each case at values between −90 to +10 mV and increased in 10 mV intervals (8.d). The currents arising in a cell with this voltage range are presented in 8a–8c. In 8a, the base current of an untreated cell is shown (control). Through treatment with sDIDS, the conductivity of the cytomembrane of this cell increases together with the current (8b). After sDIDS was removed from the experiment (post control), the conductivity of the cytomembrane of this cell decreases, together with the current (8c). In 8e, the current is plotted against the applied potential, so that the slope of the curve is a measurement of the conductivity.

The novel channel protein enables ions such as, for example: iodide, bromide, chloride, fluoride, gluconate, rhodanate and taurine to pass. Moreover, this channel protein is dependent on CFTR, since in blood cells of CF patients with sDIDS no conductivity of ions such as, for example: is iodide, bromide, chloride, fluoride, gluconate, rhodanate and taurine, can be activated.

Here this conductivity is denominated as "SDIDS activatable anion channel", abbreviated SDAC, and hereinafter named SDAC.

The past appraisal of blood of healthy persons, mucoviscidosis patients and postnatal umbilical cord blood samples of newborns (umbilical cord-blood) confirm the easy practicability and the good explanatory power of the test method according to the invention.

The method according to the invention is preferably practiced with blood cells. The use of reticulocytes and young erythrocytes is especially advantageous.

Reticulocytes are the progenitor cells of the red blood corpuscles, erythrocytes. They are produced in the bone marrow and are named reticulocytes from the moment they enter the blood circulation. They possess cell organelles and membrane transport systems. After approximately three days, the reticulocytes mature into young erythroytes by loss of their cell organelles and a part of their membrane transport systems. Erythrocytes stay in the blood circulation approximately 100 days and continually lose, in the course of this time, their membrane bound proteins. Since erythrocytes have no cell nucleus, the new synthesis of proteins is not possible. The portion of the reticulocytes in the whole blood amounts to 0.4 to 2% of the blood cells in adults and up to 10% in newborns.

The method according to the invention—influencing the volume regulation of red blood cells by blocking transmembrane proteins or initiating a high volume increase and lysis of the non-defective blood cells by an activation of CFTR-dependent ion channels—can be applied for a multiplicity of further examination methods for identifying other channel defects as, for example, the Bartter Syndrome. The Bartter Syndrome is a hereditary, kidney damaging illness, that can lead to paralysis, overhydration and general weakening of the body.

Compared to standard methods the method according to the invention has the advantage that it is fast and easy applicable with high sample throughput and thus is cost efficient. The sample material, in the form of small quantities of patient blood, is easily available and can be obtained and processed with the common facilities and instruments of a hospital laboratory. With postnatal umbilical blood, newborn screening can take place without invasive action.

A first preferred embodiment of the invention:

In accordance with the invention, first blood cells are extracted from whole blood by centrifugation. The blood cells are washed once in isotonic salt solution and are afterwards resuspended in a solution consisting of 155 mM KCl, 10 mM HEPES-Puffer (4-(2-hydroxyethyl)piperazine-1-ethanesulfonic acid), (pH 7.4) and 100 mM $GdCl_3$. This solution is incubated for 60 min under agitation at 37° C. and afterwards the released hemoglobin in the solution is determined. The reticulocytes and the new red blood corpuscles from the blood of healthy volunteers burst and release their hemoglobin; they undergo hemolysis under the specified conditions. The hemolysis is determined by visual examination and is quantified by absorption measurement with a wave length of 546 nm. In addition, a reticulocyte count can also be carried out. Performing the method by each individual practicing doctor, who possibly doesn't have the equipment of a hospital laboratory, thereby becomes practicable.

Through the described use of the $Gd^{3+}$ as inhibitor of the ATP release, an affordable and easy to handle chemical is provided. The test can deliver a reliable result within an hour. The working time and material expenditure are especially low in this case.

By choosing the conditions of the preferred embodiment of the method according to the invention, chloride ions flow into the blood cell. Healthy blood cells react thereon with an autocrine signal-cascade, that is started by the CFTR dependent ATP release and leads to the delivery of osmolytes. Influx and Efflux are at equilibrium. This CFTR dependent ATP release can be inhibited through the addition of the chemical gadolinium chloride ($GdCl_3$), which results in an accumulation of chloride within the cells. Alternatively, also other inhibitors of this ATP release, for example lanthanum ions ($La^{3+}$) in the form of lanthanum chloride ($LaCl_3$) and other inhibitors of stretch activatible cation channels, stretch activatable cation channel, SAC, allow the start of this ATP release. The water influx associated with the ion influx leads to bursting of the healthy blood cells. The hemolysis can be detected photometrically.

A second preferred embodiment of the invention:

This embodiment is carried out analogously to the example mentioned above, only the blood cells are resuspended in a solution consisting of 155 mM KCl, 10 mM HEPES-Puffer (pH 7.4) and 100 μM sDIDS. This solution is incubated for 60 min under agitation at 37° C. and afterwards the released hemoglobin in the solution is determined.

Through the selected conditions of the preferred embodiment of the method according to the invention, chloride ions flow into non-defective blood cells via the anion channel activated by sDIDS into the blood cell. That leads to the accumulation of chloride ions in the blood cell and the water influx associated ion influx leads the good blood cell to burst. The hemolysis can be detected photometrically. This procedure may also be carried out with 10 mM HEPES-buffered solution (pH 7,4), that contains 155 mM iodide, bromide, fluoride, gluconate, or rhodanate as anions.

The application of the CF tests is also possible in whole blood. Therewith the test method achieves greater application possibilities, since it can be carried out even more simply and quickly.

A particular advantage of the described tests lies in the possibility to provide for the first time, to distinguish a healthy CFTR protein functionally from a mutated, sick CFTR protein, as well as to reliably detect heterozygous CFTR mutations, that lead to physiological changes. In comparison to genetic analysis, the method according to the invention is a functional test, more economical and allows due to its fast practicability high test throughputs, which is particularly important for screening.

In the context of newborn screenings through the method of the invention, the consequential damage and thus the consequential expenses of cystic fibrosis can be limited and a meaningful risk assessment can be carried out for the concerned patient. By the earliest possible diagnosis, pathological changes of the lung and the digestive tract can be avoided or at least influenced in its development, since in the first year of life severe complications due to intestinal disturbances frequently have a lethal outcome. In advanced ages, death as a result of lung failure, including heart failure, through the overstrain of lung circulation increases. In addition, timely commenced therapy and the avoidance of the administration of inappropriate antibiotics allow a clear improvement of the quality of life and consequently an increase of the life expectancy of CF Patients.

Shown in the figures:

FIG. 1: Statistical evaluation of the experiments according to the invention, when $Gd^{3+}$ was used for blockade of the volume regulation.

FIG. 2: Statistical evaluation of the experiments according to the invention, when sDIDS was used for activating ion-channels.

FIG. 3: Mass spectrum of the improperly stored solution of DIDS in DMSO (0.1 M).

Figure 4:
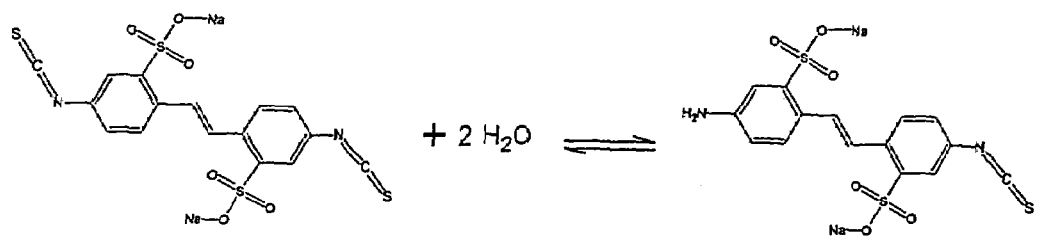

FIG. 4: Partial hydrolysis of DIDS
FIG. 5: Partial hydrolysis of SITS
FIG. 6: Polymerization of DIDS and 4-amino-4' isothiocyanato-stilbene-2,2'-disulfonic acid
FIG. 7: 4-amino4'-isothiocyanato-dihydrostilbene-2,2'-disulfonic acid, disodium salt,
FIG. 8: current and voltage ratio of Calu-3 cells, measured with the patch-clamp-technique in the whole-cell configuration.

The invention claimed is:

1. A method for the diagnosis of cystic fibrosis transmembrane conductance regulator (CFTR) defects in patients comprising the following steps:
    obtaining blood cells from the patient;
    destabilising CFTR dependent volume regulation of the obtained cells; and
    identifying CFTR defects by determining the volume of the destabilized blood cells wherein a volume increase of the destabilized cells indicates CFTR intact cells and no volume increase of the destabilized cells indicates CFTR defective cells.

2. A method for the diagnosis of CFTR defects according to claim 1, wherein the step of destabilising CFTR dependent volume regulation comprises activating or inhibiting a CFTR dependent membrane channel.

3. A method for the diagnosis of CFTR defects according to claim 2, wherein an inhibitor of ATP-release is used for inhibiting the volume regulation.

4. A method for the diagnosis of CFTR defects according to claim 2, wherein an inhibitor for stretch activatable cation channels (SAC) is used for inhibiting the volume regulation.

5. A method for the diagnosis of CFTR defects according to claim 4, wherein the inhibitor is $Gd^{3+}$.

6. A method for the diagnosis of CFTR defects according to claim 2, wherein the CFTR dependent membrane channel is activated by means for activating a CFTR dependent ion channel which is a 4-amino-4'-isothiocyanato-stilbene-2,2'-disulfonic acid (sDIDS) activatable anion channel (SDAC).

7. A method for the diagnosis of CFTR defects according to claim 6, wherein a stilbene derivative is the means for activating.

8. A method for the diagnosis of CFTR defects according to claim 7, wherein 4-amino-4'-isothiocyanato-stilbene-2,2'-disulfonic acid or derivatives is the means for activating.

9. A method for the diagnosis of CFTR defects according to claim 1, wherein the CFTR defect diagnosed is cystic fibrosis, and additionally including the steps of determining the Quantity of CFTR defective cells and of determining the degree of severity of the cystic fibrosis on the basis of the quantity of CFTR defective cells determined.

10. A method for the diagnosis of CFTR defects according to claim 1, wherein the patient is a newborn.

11. A method for the diagnosis of cystic fibrosis transmembrane conductance regulator (CFTR) defects in patients comprising the following steps:
    obtaining cells from the patient;
    destabilising CFTR dependent volume regulation of the obtained cells; and
    identifying CFTR defects by determining lysis of the destabilized cells, lysis of the destabilized cells indicating CFTR intact cells and nonlysis of the destabilized cells indicating CFTR defective cells.

12. A method for the diagnosis of CFTR defects according to claim 11, wherein an optical procedure is used for quantifying the lysis.

13. A method for the diagnosis of CFTR defects according to claim 11, wherein the cells obtained from the patient are blood cells contained in a smear and wherein the lysis is quantified by reticulocyte count in the smear.

14. A method for the diagnosis of CFTR defects according to claim 11, wherein the cells obtained from the patient are blood cells.

15. A method for the diagnosis of CFTR defects according to claim 11, wherein the patient is a newborn.

16. A method for the diagnosis of CFTR defects according to claim 11, wherein the step of destabilising CFTR dependent volume regulation comprises activating or inhibiting a CFTR dependent membrane channel.

17. A method for the diagnosis of CFTR defects according to claim 16, wherein an inhibitor of ATP-release is used for inhibiting the volume regulation.

18. A method for the diagnosis of CFTR defects according to claim 16, wherein an inhibitor for stretch activatable cation channels (SAC) is used for inhibiting the volume regulation.

19. A method for the diagnosis of CFTR defects according to claim 18, wherein the inhibitor is $Gd^{3+}$.

20. A method for the diagnosis of CFTR defects according to claim 16, wherein the CFTR dependent membrane channel is activated by means for activating a CFTR dependent ion channel which is a 4-amino-4'-isothiocyanato-stilbene-2,2'-disulfonic acid (sDIDS) activatable anion channel (SDAC).

21. A method for the diagnosis of CFTR defects according to claim 20, wherein a stilbene derivative is the means for activating.

22. A method for the diagnosis of CFTR defects according to claim 21, wherein 4-amino-4'-isothiocyanato-stilbene-2,2'-disulfonic acid or derivatives is the means for activating.

* * * * *